(12) United States Patent
Mackewitz et al.

(10) Patent No.: US 8,106,220 B2
(45) Date of Patent: *Jan. 31, 2012

(54) PREPARATION OF PHTHALIC ANHYDRIDE BY GAS PHASE OXIDATION OF O-XYLENE IN A MAIN REACTOR AND POSTREACTOR

(75) Inventors: Thomas Mackewitz, Mannheim (DE); Frank Rosowski, Mannheim (DE); Andreas Tenten, Neustadt/Weinstraβe (DE)

(73) Assignee: BASF SE, Ludwigshafen (DE)

( * ) Notice: Subject to any disclaimer, the term of this patent is extended or adjusted under 35 U.S.C. 154(b) by 211 days.

This patent is subject to a terminal disclaimer.

(21) Appl. No.: 12/301,370

(22) PCT Filed: May 18, 2007

(86) PCT No.: PCT/EP2007/054839
§ 371 (c)(1),
(2), (4) Date: Nov. 18, 2008

(87) PCT Pub. No.: WO2007/135102
PCT Pub. Date: Nov. 29, 2007

(65) Prior Publication Data
US 2009/0156835 A1    Jun. 18, 2009

(30) Foreign Application Priority Data
May 19, 2006  (EP) .................................. 06010416

(51) Int. Cl.
*C07D 307/89* (2006.01)
(52) U.S. Cl. ........................................................ 549/248
(58) Field of Classification Search .................. 549/248, 549/249
See application file for complete search history.

(56) References Cited

U.S. PATENT DOCUMENTS

| | | | |
|---|---|---|---|
| 5,969,160 A | 10/1999 | Lindstrom | |
| 7,390,911 B2 * | 6/2008 | Neto et al. | 549/249 |
| 2008/0177105 A1 | 7/2008 | Raichle et al. | |
| 2008/0214863 A1 | 9/2008 | Cremer et al. | |
| 2008/0307648 A1 | 12/2008 | Cremer et al. | |
| 2008/0312477 A1 | 12/2008 | Raichle et al. | |
| 2009/0156835 A1 | 6/2009 | Mackewitz et al. | |
| 2009/0163726 A1 | 6/2009 | Wilmer et al. | |
| 2009/0171101 A1 | 7/2009 | Lautensack et al. | |
| 2009/0198073 A1 * | 8/2009 | Mackewitz et al. | 549/248 |
| 2009/0270640 A1 | 10/2009 | Maurer et al. | |
| 2009/0318712 A1 | 12/2009 | Wilmer et al. | |
| 2010/0029955 A1 | 2/2010 | Wilmer et al. | |
| 2011/0034707 A1 | 2/2011 | Wilmer et al. | |

FOREIGN PATENT DOCUMENTS

| | | |
|---|---|---|
| DE | 20 05 969 A1 | 8/1971 |
| DE | 198 07 018 A1 | 8/1998 |
| DE | 19823262 | 12/1999 |
| DE | 19823275 | 12/1999 |
| DE | 10040827 | 3/2002 |
| DE | 10110847 | 9/2002 |
| DE | 101 44 857 A1 | 3/2003 |
| DE | 10206989 | 8/2003 |
| DE | 102004061770 | 7/2006 |
| WO | WO-02/16299 A | 2/2002 |
| WO | WO-03/070680 A | 8/2003 |
| WO | WO 2005/012216 | 2/2005 |
| WO | WO-2008/022909 A1 | 2/2008 |
| WO | WO-2008/022911 A1 | 2/2008 |
| WO | WO-2009/021924 A1 | 2/2009 |
| WO | WO-2009/124947 A1 | 10/2009 |

* cited by examiner

*Primary Examiner* — Taylor Victor Oh
(74) *Attorney, Agent, or Firm* — Connolly Bove Lodge & Hutz LLP

(57) ABSTRACT

A process is described for preparing phthalic anhydride by catalytic gas phase oxidation of o-xylene, in which a gaseous mixture of o-xylene and an oxygenous gas is converted in a main reactor to a gaseous intermediate reaction product which comprises unconverted o-xylene, phthalic anhydride underoxidation products and phthalic anhydride, the heat of reaction which arises in the main reactor being removed at least partly by indirect cooling with a heat carrier medium, and the intermediate reaction product being introduced into a postreactor. The concentration of unconverted o-xylene in the intermediate reaction product is at least 1% by weight, and the sum of the concentrations of phthalic anhydride underoxidation products in the intermediate reaction product is at least 0.5% by weight. The process allows an increase in the overall yield of phthalic anhydride without or without significant deterioration in the product quality.

17 Claims, No Drawings

PREPARATION OF PHTHALIC ANHYDRIDE BY GAS PHASE OXIDATION OF O-XYLENE IN A MAIN REACTOR AND POSTREACTOR

This application is a national phase of PCT/EP2007/054839, filed on May 18, 2007 which claims priority to EP 06010416.3 filed May 19, 2006, the entire contents of all are hereby incorporated by reference.

The present invention relates to a process for preparing phthalic anhydride by gas phase oxidation of o-xylene in a main reactor and a downstream postreactor.

The gas phase oxidation of o-xylene and/or naphthalene to phthalic anhydride (PA) is well known and described many times in the literature. A review is given, for example, by H. Suter, Phthalsäureanhydrid und seine Verwendung [Phthalic anhydride and its use], Steinkopf Verlag, Darmstadt, 1972, or F. K. Towae, W. Enke, R. Jäckh, N. Bhargava in Ulimann's Encyclopedia of Industrial Chemistry, Vol A20, 1992, p. 181-190.

In general, the oxidation reaction of o-xylene is effected under air in a tube bundle reactor temperature-controlled with a salt melt. In this case, virtually complete conversion of the hydrocarbon used in the reactor and simultaneously a high product quality of the phthalic anhydride formed are desired, in order to achieve this on the one hand but simultaneously to avoid damage to the catalyst as a result of high hotspot temperatures, catalysts of different activity are generally arranged layer by layer in the tubes, the less active catalyst generally being arranged in the fixed bed such that the reaction mixture comes into contact with it first while the most active catalyst is disposed toward the gas outlet from the catalyst bed. Such activity structures of the catalyst are described, for example, by DE 198 23 262, DE 198 23 275, DE 100 40 827 and DE 102 08 989.

However, especially in the case of relatively high hydrocarbon loadings it becomes increasingly difficult to obtain sufficiently good product quality without yield losses in the reactor as a result of total oxidation to CO and $CO_2$, since the most active but least selective catalyst layer at the gas outlet of the catalyst bed here must make a relatively high contribution to the overall conversion. This effect also occurs over time as a result of the slow deactivation of the generally highly stressed selective layer or selective layers at the gas inlet of the catalyst bed.

One means of overcoming the above-described difficulties consists in the use of two separate reactors instead of a single reactor. For example, DE 20 05 988 describes a process for preparing phthalic anhydride in two separate reactors. The first reactor is a salt-bath-cooled and largely isothermically operated tube bundle reactor, while the second reactor is an adiabatically operated shaft furnace. The reaction in the first reactor is conducted in such a way that from 1 to 20% by weight of the hydrocarbon used remains unchanged. The process is further characterized in that the temperature-$T_1$ of the heat exchange medium in the first reactor is between 380 and 430° C. and the entrance temperature $T_2$ of the adiabatically operated second reaction stage obeys the relationship $T_2=T_1-5$ to 150° C.

The process described in DE 198 07 018 and U.S. Pat. No. 5,989,180 comprises at least two separate reactors, the first reactor being a salt bath-cooled main reactor and the second reactor a postreactor without cooling equipment and with the same catalyst or a different catalyst. The product gas stream in the postreactor is from the fop downward. The process enables the temperature in the main reactor to be lowered in the direction toward underoxidation conditions, which is why the phthalide values in the main reactor outlet and postreactor inlet are in the range from 0.5 to 0.9% by weight. These conditions are controlled by the observation of the o-xylene content at the main reactor outlet and postreactor inlet, which should explicitly be less than 100 ppm (0.01% by weight).

A further postreactor design is described in H.-J. Eberle, J. Breimair, H. Domes, T. Gutermuth, PTQ Summer 2000, 129-133, Here, a postreactor with a honeycomb catalyst is connected downstream of the salt bath-cooled tube bundle reactor which comprises a multilayer catalyst, the product stream being cooled to the desired entrance temperature by means of a product gas cooler before it enters the postreactor zone. The postreactor serves primarily to comply with a predetermined quality of the phthalic anhydride obtained, especially in the case of high o-xylene loadings and in the case of aged main reactor catalysts. The o-xylene concentration at the postreactor inlet, with a main reactor catalyst which has reached the end of its lifetime, is about 0.85-0.70% by weight of the sum of the organic components in the product gas stream, and the concentration of underoxidized secondary components such as phthalide or o-tolylaldehyde is 0.20-0.50% by weight of the sum of the organic components in the product gas stream.

It is an object of the invention to increase the total yield of phthalic anhydride without or without significant deterioration in the product quality.

The object is achieved by a process for preparing phthalic anhydride by catalytic gas phase oxidation of o-xylene, in which a gaseous mixture of o-xylene and an oxygenous gas is converted in a main reactor to a gaseous intermediate reaction product which comprises unconverted o-xylene, phthalic anhydride underoxidation products and phthalic anhydride, the heat of reaction which arises in the main reactor being removed at least partly by indirect cooling with a heat carrier medium, and the intermediate reaction product being introduced into a postreactor with a temperature which is lower than the lowest temperature of the heat carrier medium, wherein the concentration of unconverted o-xylene in the intermediate reaction product is at least 1% by weight, and the sum of the concentrations of phthalic anhydride underoxidation products in the intermediate reaction product is at least 0.5% by weight, based in each case on the total weight of the organic components in the intermediate reaction product.

Phthalic anhydride underoxidation products are understood to mean Ce species which have a lower oxidation state than phthalic anhydride and are oxidizable further to phthalic anhydride. These include in particular o-tolylaldehyde, o-toluic acid and phthalide.

Typically, the concentration of unconverted o-xylene in the intermediate reaction product is from 1.2 to 5.0% by weight, more preferably from 1.4 to 2.0% by weight.

The sum of the concentrations of o-tolylaldehyde and phthalide in the intermediate reaction product is preferably at least 0.5% by weight, for example from 0.8 to 1.5% by weight, more preferably from 0.7 to 1.3% by weight.

The concentration of o-tolylaldehyde in the intermediate reaction product is preferably at least 0.25% by weight, in particular from 0.35 to 0.6% by weight.

The concentration of phthalide in the intermediate reaction product is preferably at least 0.25% by weight, in particular from 0.35 to 0.6% by weight.

In general, the weight ratio of unconverted o-xylene to o-tolylaldehyde in the intermediate reaction product is from 1 to 20, preferably from 2 to 10; and the weight ratio of unconverted o-xylene to phthalide is from 1 to 20, preferably from 2 to 10.

The content of o-xylene in the intermediate reaction product is preferably less than or equal to 20 $g/m^3$ (STP), more preferably less than or equal to 15 $g/m^3$.

In preferred embodiments of the process according to the invention, measurements for the concentration of o-xylene in the intermediate reaction product are obtained continuously or at time intervals, for example at least once per week or at least once daily, and control interventions for the temperature of the heat carrier medium are formed from the measurements. For instance, the temperature of the heat carrier medium can be lowered if the concentration of o-xylene in the intermediate reaction product falls below a predefined target value or the inventive limiting value, or the temperature of the heat carrier medium can be increased if the concentration of o-xylene in the intermediate reaction product is too high.

The concentration of o-tolylaldehyde or phthalide based on the organic components in the intermediate reaction product can be determined at ambient temperature (23° C.) by condensing all components of the intermediate reaction product which are condensate at this temperature and analyzing the condensate by means of gas chromatography in a suitable solvent such as acetone. Carbon monoxide and/or carbon dioxide which may be present in the intermediate reaction product do not count as organic components of the intermediate reaction product.

The main reactor used is preferably a salt bath-cooled tubular reactor. This comprises a tube bundle flowed around by a heat carrier medium in the form of a sail bath. The individual catalyst-filled tubes end in an upper tube plate and a lower tube plate. The reaction gas is generally passed from the top downward, i.e. in the direction of gravity, through the tube; however, a reverse flow direction is also conceivable. Spaced apart on the jacket of the reactor are annular channels through which the heat carrier medium can be drawn off from the reactor and fed back to the reactor after passing through a circulation pump. A substream of the circulated heat carrier medium is passed through a cooler in which, for example, saturated steam is produced. Guide plates may typically be present in the interior of the reactor, in order to impart a radial flow component to the heat carrier medium in the region of the tube bundle.

The temperature difference of the heat carrier medium between reactor inlet and outlet may be from 0.5 to 12° C., usually from 1 to 8° C. The heat carrier medium may, in relation to the reaction gas, pass through the tubular reactor either in cocurrent or in countercurrent. Moreover, the tubular reactor may comprise a plurality of reaction zones with separate or connected circuits of the heat carrier medium. The "lowest temperature of the heat carrier medium" refers to the lowest temperature that the heat carrier medium has at a point within the reactor jacket (typically close to the entry point of the heat carrier medium coming from the circulation pump into the reactor). When the reactor comprises a plurality of reaction zones, the relevant zone will be the one operated at the lowest temperature.

The main reactor is typically operated with a temperature of the heat carrier medium of from 320 to 390° C. The gas temperature in the main reactor is in the range from 340 to 460° C., more preferably in the range from 360 to 435° C.

The reaction gas supplied to the catalyst is generally obtained by mixing a gas which comprises molecular oxygen and, apart from oxygen, may also comprise suitable reaction moderators and/or diluents such as steam, carbon dioxide and/or nitrogen with o-xylenes and the oxygenous gas may comprise generally from 1 to 100 mol %, preferably from 2 to 50 mol % and more preferably from 10 to 30 mol % of oxygen, from 0 to 30 molts, preferably from 0 to 10 mol % of steam, and from 0 to 50 mol %, preferably from 0 to 1 mol % of carbon dioxide, remainder nitrogen. The oxygenous gas is generally air.

The o-xylene loading of the gaseous mixture entering the main reactor is generally from 30 to 150 g per m$^3$ (STP) of gas, preferably at least 80 g/m$^3$ (STP), for example from 75 to 120 g/m$^3$ (STP).

The main reactor is filled with one catalyst or successive layers of different catalysts which are suitable for the catalysis of the gas phase oxidation of o-xylene to phthalic anhydride. They are preferably coated or spherical catalysts, on whose core of an inert, support material are applied one or more layers of catalytically active metal oxides.

In the main reactor, preference is given to using catalysts whose activity is reduced in favor of a higher selectivity. Selectivity is understood here to mean the selectivity with regard to the sum of phthalic anhydride and all $C_5$ species which are oxidizable further to phthalic anhydride, in activity-structured catalyst beds, such as those mentioned at the outset, these are generally the catalysts placed toward the gas inlet side. They are frequently referred to as "selective catalysts", in contrast to the "active catalysts" placed toward the gas outlet side. The main reactor comprises preferably only one or more selective catalyst layers and no typical active catalyst layer. Although this results in higher concentrations of unconverted o-xylene and underoxidized secondary components in the intermediate reaction product, the oxidation of o-xylene to phthalic anhydride (or to $C_8$ species which are oxidizable to phthalic anhydride in the postreactor) can be operated more selectively in the main reactor. Thus, the temperature of the heat carrier medium can be adjusted better in the case of an aging catalyst, since the catalyst layer or the catalyst layers in the main reactor—unlike in the case of a bed composed of selective and active catalysts—only differ slightly with regard to their activities.

Typical such selective catalysts, which are preferably used exclusively in the main reactor, are a) one or more catalysts whose active composition is a mixed multimetal oxide comprising silver, vanadium and if appropriate one or more promoter metals, in particular a silver vanadium oxide bronze, and/or b) one or more catalysts based on vanadium oxide and titanium dioxide, in which the alkali metal content of the active composition is greater than or equal to 0.12% by weight and the phosphorus content of the active composition (calculated as p) is less than or equal to 0.20% by weight, and c) combinations of one or more catalysts according to the above definition a) and one or more catalysts according to the above definition b).

Mixed multimetal oxides which comprise silver, vanadium and if appropriate one or more promoter metals, and also silver vanadium oxide bronzes and their preparation, are known per se, for example from WO 00/27753, WO 01/85337 and WO 2005/012218. Silver vanadium oxide bronzes are understood to mean silver vanadium oxide compounds with an atomic Ag:V ratio of less than 1. They are generally semiconductive or metallically conducting oxidic solids which preferably crystallize in layer or tunnel structures, the vanadium in the [$V_2O_5$] host lattice being present partly in reduced from to V(IV). Silver vanadium oxide bronzes form above 200° C., especially at temperatures of more than 300° C., by decomposition of the mixed multimetal oxides.

Suitable mixed multimetal oxides are, for example, those of the general formula I $$Ag_{a-c}M^1_cV_2O_d * eH_2O, \qquad\qquad I$$

in which
a is from 0.3 to 1.0,
$M^1$ is at least one metal selected from alkali metals and alkaline earth metals, Bi, Tl, Cu, Zn, Co, Pb, Or, Au, Ai, Fe, Co, Ni, Mo, Nb, Ce, W, Mn, Ta, Pd, Pt, Ru and/or Rh,
c is from 0 to 0.5, with the proviso that (a-c) is $\geq 0.1$, d is a number which is determined by the valency and frequency of the elements other than oxygen in the formula I, and e is from 0 to 20, preferably from 0 to 5.

In the multimetal oxide of the formula I, the variable A is preferably from 0.5 to 1.0 and more preferably from 0.6 to 0.9, the variable b is preferably from 0 to 0.1, and the variable c is preferably from 0.005 to 0.2, in particular from 0.01 to 0.1.

The number d is determined from the valency and frequency of the elements other than oxygen in the multimetal oxide of the formula I. The number e, which is a measure of the wafer content, is preferably from 0 to 5.

$M^1$ is preferably Na, K, Rb, Tl, Ni, W, Co, Fe, Mo, Nb, Zn, Ce and Mn.

Particular preference is given to multimetal oxides of the general formula Ia

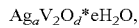  Ia in which
a is from 0.6 to 0.9,
d is as defined above, and
e is from 0 to 5.

To prepare the multimetal oxides, a suspension of vanadium pentoxide ($V_2O_5$) is generally heated with the solution of a silver compound and, if appropriate, a solution of a compound of the metal component $M^1$ and a compound of Q. The solvent used for this reaction is preferably water. The silver salt used is preferably silver nitrate; the use of other soluble silver salts, for example silver acetate, silver perchlorate or silver fluoride, is likewise possible.

The salts of the metal component $M^1$-selected are generally those which are soluble in the solvent used. When water is used as the solvent in the preparation of the inventive multimetal oxides, it is possible, for example, to use the perchlorates or carboxylates, especially the acetates, of the metal component $M^1$. Preference is given to using the nitrates of the metal component $M^1$ in question.

According to the desired chemical composition of the multimetal oxide of the formula I, it is prepared by reacting the amounts of $V_2O_5$, silver compound and the compound of the metal component $M^1$ which are calculated from a and c of formula I with one another. The multimetal oxide thus formed can be isolated from the reaction mixture and stored until further use. Particularly advantageously, the isolation of the resulting multimetal oxide suspension is performed by means of spray-drying. The spray-dried powder is then applied to an inert support.

Catalysts based on vanadium oxide and titanium dioxide comprise vanadium pentoxide in addition to titanium dioxide (in the form of its anatase modification). Typical catalysts based on vanadium oxide and titanium dioxide and their preparation are described in DE 198 23 282.

The catalyst based on vanadium oxide and titanium dioxide in the calcined state preferably comprises from 1 to 20% by weight of vanadium oxide, calculated as $V_2O_5$, and from 80 to 98% by weight of titanium dioxide calculated as $TiO_2$. In addition, small amounts of a multitude of other oxidic compounds may be present, which, as promoters, influence the activity and selectivity of the catalysts. The activity-reducing and selectivity-increasing promoters used are generally alkali metals such as cesium, lithium, potassium and rubidium, and especially cesium.

The activity-increasing additives used are generally phosphorus compounds. In the selective catalysts, at most small additions, if any, of phosphorus compounds are used.

The catalysts based on vanadium oxide and titanium dioxide may also comprise antimony compounds.

The components are used in the form of their oxides or in the form of compounds which are converted to oxides in the course of heating, or in the course of heating in the presence of oxygen. The vanadium components used may be vanadium oxides or vanadium compounds which are converted to vanadium oxides in the course of heating, individually or in the form of their mixtures. Preference is given to using $V_2O_5$ or $NH_4VO_3$. It is also possible to additionally use a reducing agent, such as formic acid or oxalic acid, in order to reduce the vanadium (V) compound at least partly to vanadium (IV). Suitable promoter (precursor) compounds are the corresponding oxides, or compounds which are converted to oxides after heating, such as sulfates, nitrates, carbonates. Suitable examples are $Na_2CO_3$, $K_2O$, $Cs_2O$, $Cs_2CO_3$, $Cs_2SO_4$, $P_2O_5$, $(NH_4)_2HPO_4$, $Sb_2O_3$.

The active composition is formed generally by preparing an aqueous slurry of the compound of the vanadium component, of the titanium dioxide and of promoter (precursor) compounds in suitable amounts, and stirring the slurry until sufficient homogenization is achieved. The slurry can then be spray-dried or be used as such for the coating.

The catalysts used in the process according to the invention are generally coated catalysts in which the catalytically active composition is applied in coating form on an inert support. The layer thickness of the catalytically active composition is generally from 0.02 to 0.2 mm, preferably from 0.05 to 0.1 mm. In general, the catalysts have an active composition layer with essentially homogeneous chemical composition applied in coating form.

The inert support materials used may be virtually all known support materials, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The support material is generally nonporous. Advantageous support materials which should be emphasized are in particular steatite and silicon carbide. The shape of the support material is generally uncritical. For example, catalyst supports can be used in the form of spheres, rings, tablets, spirals, tubes, extrudates or spall. The dimensions of these catalyst supports correspond to those of catalyst supports typically used to prepare coated catalysts for the gas phase partial oxidation of aromatic hydrocarbons. Preference is given to using steatite in the form of spheres having a diameter of from 3 to 8 mm or of rings having an external diameter of from 5 to 9 mm and a length of from 4 to 7 mm.

The active composition layer can be applied to the support by any methods known per se, for example by spraying solutions or suspensions in a coating drum, or coating with a solution or suspension in a fluidized bed. It is possible for organic binders, preferably copolymers, advantageously in the form of an aqueous dispersion, of vinyl acetate/vinyl laurate, vinyl acetate/acrylate, styrene/acrylate, vinyl acetate/maleate, vinyl acetate/ethylene and hydroxyethylcellulose to be added to the catalytically active composition, the amounts of binder used advantageously being from 3 to 20% by weight, based on the solids content of the solution of the active composition constituents. The binders applied burn off within a short time after the introduction of the catalyst and startup of the reactor. The binder addition additionally has the advantage that the active composition adheres efficiently on the support, so as to facilitate transport and filling of the catalyst.

The gaseous intermediate reaction product which leaves the main reactor is fed to a postreactor. It forms the exclusive feed to the postreactor, i.e. no gases, such as fresh or waste air or o-xylene, are added to the intermediate reaction product.

Useful postreactors are all reactors which are suitable for performing heterogeneously catalyzed gas phase reactions, especially fixed bed reactors with a fixed catalyst bed, tube bundle reactors, reactors with catalyst-coated monolithic honeycombs and the like. They may be vertical or horizontal designs; the flow toward vertical reactors may be from the bottom or from the top.

The intermediate reaction product enters the postreactor with a temperature which is lower than the lowest temperature of the heat carrier medium in the main reactor. It is usually preferred that the intermediate reaction product which leaves the main reactor is cooled by means of a suitable cooling stage before it enters the postreactor. The difference between the exit temperature from the main reactor and the entrance temperature into the postreactor is preferably at least 5° C. In particular at least 10° C. The performance of the cooling stage is appropriately controlled as a function of the o-xylene concentration in the intermediate reaction product and the activity of the postreactor catalyst such that the phthalic anhydride yield and purity are maximized.

The main reactor, the cooling stage and the postreactor may be arranged in separate apparatus. Suitable cooling stages are liquid-cooled indirect heat exchangers or gas-gas heat exchangers, by means of which the reaction gas fed to the main reactor can be preheated.

Alternatively, it is also possible to combine main reactor and cooling stage, or cooling stage and postreactor, in a single apparatus. For example, the cooling stage can be designed as an immediate extension of the reaction tubes of the main reactor, which, in the region of the cooling stage, are not filled with catalyst and are cooled by means of a separate circuit of a heat carrier medium or with a substream of the heat carrier medium coming from the cooler.

It is also possible for the functions of the main reactor, of a cooling stage and of the postreactor to be arranged in a single casing, as described in DE 101 44 857.

The design of the postreactor depends upon its operating mode. In one possible embodiment, the postreactor is operated essentially adiabatically.

In another possible embodiment, at least some of the heat of reaction which arises in the postreactor is removed by indirect cooling with a heat carrier medium. Suitable heat carrier media for the postreactor are heat carrier oils, salt melts, air or wafer. Typical cooling processes can be found in the patent application DE 10 2004 061770 which has an earlier priority date than the present application. Particular preference is given to a design in which the reaction gas flows first through an adiabatic catalyst layer and then through a catalyst layer disposed between thermoplates.

The postreactor catalysts used are preferably coated or spherical catalysts, on whose core of an inert support material are applied one or more layers of catalytically active metal oxides. Typical support materials and typical metal oxides and promoters used can be found in DE 198 23 282. Preference is given to using catalysts which are different form the catalysts used in the main reactor. Preference is given to using "active catalysts". Therefore, preference is given to using, in the postreactor, at least one catalyst based on vanadium oxide and titanium dioxide, in which the alkali metal content of the active composition is less than or equal to 0.20% by weight.

Optionally, the active composition comprises phosphorus; the phosphorus content of the active composition is, for example, greater than or equal to 0.12% by weight.

The postreactor is typically operated at gas temperatures of from 240 to 380° C., more preferably from 270 to 350° C. The highest gas temperature which occurs in the postreactor is preferably at least 30° C. lower, in particular at least 40° C. lower, and the highest gas temperature which occurs in the main reactor.

In general, the reaction gas which leaves the postreactor is cooled in a product gas condenser and the phthalic anhydride is deposited out of the hot reaction gases in a customary manner by means of phthalic anhydride separators operated in alternation. Optionally, a so-called liquid separator can be connected upstream of the separators, which is advantageous particularly at high loadings.

The process according to the invention can also be applied to the preparation of other products by catalytic gas phase oxidation, for example phthalic anhydride from naphthalene or o-xylene/naphthalene mixtures, acrylic acid from propene, maleic anhydride from benzene, butane, butene or butadiene, benzoic acid from toluene, etc.

The invention is illustrated in detail by the examples and comparative examples which follow.

EXAMPLES

Preparation of the Catalysts

Preparation of the Main Reactor Catalyst I (Selective Catalyst)

After stirring for 18 hours, 238.8 g of a suspension consisting of 104.9 g of oxalic acid, 39.4 g of vanadium pentoxide, 17.0 g of antimony oxide, 2.87 g of cesium sulfate, 3.15 g of ammonium dihydrogenphosphate, 149.0 g of formamide, 465.9 g of titanium dioxide of the anatase modification having a SET surface area of 20 $m^2/g$, and 721.0 g of water are applied in a coating drum at 160° C. together with 13.0 g of organic binder to 1400 g of steatite rings of dimensions 8×6×5 mm (external diameter×height×internal diameter). In a second step, the rings thus coated are coated with 236.2 g of a second suspension which had likewise been stirred beforehand for 18 h, consisting of 58.7 g of oxalic acid, 21.0 g of vanadium pentoxide, 2.87 g of cesium sulfate, 198.0 g of formamide, 501.9 g of titanium dioxide and 720.3 g of water, together with 12.8 g of organic binder.

After calcination of the catalyst at 450° C. for one hour, the active composition applied to the steatite rings is 9.3%. The active composition has the composition of 5.75% $V_2O_5$, 1.6% $Sb_2O_3$, 0.40% Cs, 0.08% P, remainder $TiO_2$.

Preparation of the Main Reactor Catalyst II (Active Catalyst)

After stirring for 18 hours, 538.0 g of a suspension consisting of 106.4 g of oxalic acid, 39.4 g of vanadium pentoxide, 17.0 g of antimony oxide, 0.83 g of cesium sulfate, 3.35 g of ammonium dihydrogenphosphate, 149.6 g of formamide, 467.5 g of titanium dioxide of the anatase modification having a BET surface area of 20 $m^2/g$, and 719.1 g of water are applied in a coating drum at 180° C. to 1400 g of steatite rings of dimensions 8×6×5 mm (external diameter×height× internal diameter).

After calcination of the catalyst at 450° C. for one hour, the active composition applied to the steatite rings is 10.5%. The active composition has the composition of 7.5% $V_2O_5$, 3.2% $Sb_2O_5$, 0.09% Cs, 0.17% P, remainder $TiO_2$.

Preparation of the Main Reactor Catalyst III (Selective Catalyst with AgV Bronze)

The catalyst having an active composition of the composition $Ce_{0.02}Ag_{0.71}V_2O_x$ was pre-pared according to WO 2005/012216 (catalyst A.1), Preparation of the Postreactor Catalyst After stirring for 18 hours, 540.2 g of a suspension consisting of 105.5 g of oxalic acid, 39.4 g of vanadium pentoxide, 17.0 g of antimony oxide, 0.29 g of cesium sulfate, 8.9 g of ammonium dihydrogenphosphate, 149.0 g of formamide, 467.0 g of titanium dioxide of the anatase modification having a BET surface area of 20 $m^2 \cdot g^{-1}$, and 720.5 g of water are applied in a coating drum at 160° C. to 1400 g of steatite rings of dimensions 8×8×5 mm (external diameter×height×internal diameter).

After calcination of the catalyst at 450° C. for one hour, the active composition applied to the steatite rings is 10.8%. The active composition has the composition of 7.5% $V_2O_5$, 3.2% $Sb_2O_3$, 0.04% Cs, 0.41% P, remainder $TiO_2$.

Examples 1 to 15

The main reactor used was a tube bundle reactor with 99 normal tubes and 2 thermal tubes. The normal tubes had an internal width of 25 mm, the thermal tubes an internal width of 29 mm with sleeves (diameter 10 mm) with installed 30-point multi-element with temperature measuring points at a distance of 10 cm or with a sampling element according to DE 101 10 847, From the bottom upward, 320 cm of main reactor catalyst I were introduced into each of the 360 cm-long iron tubes. By means of pressure equalization, it was ensured that the same inlet pressure was present at each tube inlet. If appropriate, a little main reactor catalyst I was added or sucked out in the 99 normal tubes; in the two thermal tubes, the pressure equalization was achieved by adding inert material in the form of steatite spheres and quartz chips. For temperature control, the iron tubes were surrounded by a salt melt which was disposed in two separate salt baths. The lower salt bath (salt bath 8) surrounded the tubes from the lower tube plate up to a height of 140 cm; the upper salt bath (salt bath A) surrounded the tubes from the height of 140 cm up to the upper tube plate.

The postreactor (internal diameter 45 cm, height about 100 cm) was equipped at a height of about 90 cm with cooling coils (diameter 12 mm, cooling coil separation about 30 mm) which were charged in the lower part over a height of 47 cm with air at ambient temperature as the cooling medium. The postreactor was filled with postreactor catalyst up to a fill height of 85 cm.

To operate the plant, an air/o-xylene mixture was passed from the top downward through the reactor at main reactor inlet temperature about 200-205° C., then cooled to a certain postreactor inlet temperature in a heat exchanger and then passed from the top downward through the postreactor. The air cooling in the lower part of the postreactor was effected over a height of 47 cm such that a certain temperature in the catalyst bed, which was measured 10 cm above the postreactor outlet, was established. The o-xylene used had a purity of 98.5-99.0% by weight.

After a generally customary runup time of the main reactor catalyst, the results reported in table 1 were obtained.

Examples 16 to 21

A main reactor as in the above examples was used. From the bottom upward, 240 cm of main reactor catalyst I, 84 cm of main reactor catalyst III and then 12 cm of steatite rings of dimensions 8×6×5 mm (external diameter×height×internal diameter) as inert material were introduced into each of the 360 cm-long iron tubes. By means of pressure equalization, it was ensured that the same inlet pressure was present at each tube inlet.

The postreactor (internal diameter 45 cm, height about 100 cm) was equipped at a height of about 90 cm with cooling coils (diameter 12 mm, cooling coil separation about 30 mm) which were charged in the lower part over a height of 4 cm with air at ambient temperature as the cooling medium. The postreactor was filled with postreactor catalyst up to a fill height of 85 cm.

To operate the plant, an air/o-xylene mixture was passed from the top downward through the main reactor at main reactor inlet temperature about 200-205° C., then cooled to a certain postreactor inlet temperature in a heat exchanger and then passed from the top downward through the postreactor. The air cooling in the lower part of the postreactor was effected over a height of 47 cm such that a certain temperature in the catalyst bed, which was measured 10 cm above the postreactor outlet, was established.

After a generally customary runup time of the main reactor catalyst, the results reported in table 1 were obtained.

Comparative Examples 1 to 9

A main reactor as in the above examples was used. From the bottom upward, in each case 101 cm of main reactor catalyst II and then 229 cm of main reactor catalyst I were introduced into each of the 380 cm-long iron tubes. By means of pressure equalization, it was ensured that the same inlet pressure was present at each tube inlet. If appropriate, a little main reactor catalyst I was added or sucked out in the 99 normal tubes; in the two thermal tubes, the pressure equalization was achieved by adding inert material in the form of steatite spheres and quartz chips.

A postreactor as in the above examples was used; as a result of the cooling coils, however, no air was passed to the cooling.

To operate the plant, air/o-xylene mixture was passed through the main reactor from the top downward at main reactor inlet temperature about 200-205° C., then cooled to a certain postreactor inlet temperature in a heat exchanger and then passed from the top downward through the adiabatically operated postreactor. The temperature reported was measured 10 cm above the postreactor outlet. The o-xylene used had a purity of 98.5-99.0% by weight.

After a generally customary runup time of the main reactor catalyst, the results reported in table 2 were achieved.

in the tables:

run day=operating day from the first startup of the main reactor catalyst;

salt bath A=salt bath temperature* of the salt bath placed toward the reactor inlet;

salt bath B=salt bath temperature* of the salt bath placed toward the reactor outlet (*the lowest temperature of the salt bath within the reactor is reported in each case);

o-xylene MR outlet, o-tolylaldehyde MR outlet and phthalide MR outlet=o-xylene, o-tolylaldehyde and phthalide content respectively in % by weight of the organic components of the crude product gas at the main reactor outlet;

o-xylene PR outlet, o-tolylaldehyde PR outlet and phthalide PR outlet=o-xylene, o-tolylaldehyde and phthalide content respectively in % by weight of the organic components of the crude product gas at the postreactor outlet;

PA yield PR outlet=PA yield in % by weight based on 100% o-xylene from the analysis of the crude product gas in the postreactor outlet.

TABLE 1

Results of examples 1 to 15

| Example | Run day | o-Xylene [g/m³ (STP)] | Air [m³ (STP)/h per tube] | Temperature of Salt bath A Salt bath B [° C.] | Temperature of PR inlet Cat. Bed [° C.] | o-Xylene MR outlet PR outlet [% by wt.] | o-Tolylaldehyde MR outlet PR outlet [% by wt.] | Phthalide MR outlet PR outlet [% by wt.] | PA yield PR outlet [m/m %] |
|---|---|---|---|---|---|---|---|---|---|
| 1 | 60 | 63.3 | 3.8 | 350.0 | 320 | 1.41 | 0.46 | 0.47 | 116.04 |
|   |    |      |     | 350.0 | 295 | 0.04 | 0.05 | 0.09 |        |
| 2 | 66 | 65.6 | 3.8 | 349.5 | 324 | 1.63 | 0.50 | 0.47 | 115.67 |
|   |    |      |     | 349.5 | 295 | 0.04 | 0.04 | 0.07 |        |
| 3 | 99 | 62.8 | 3.8 | 350.0 | 320 | 1.04 | 0.35 | 0.34 | 115.34 |
|   |    |      |     | 350.0 | 291 | 0.01 | 0.02 | 0.03 |        |
| 4 | 101 | 65.7 | 3.8 | 349.0 | 320 | 1.50 | 0.44 | 0.41 | 115.64 |
|   |    |      |     | 349.0 | 292 | 0.04 | 0.04 | 0.06 |        |
| 5 | 103 | 66.2 | 3.8 | 349.0 | 320 | 1.51 | 0.45 | 0.42 | 115.67 |
|   |    |      |     | 349.0 | 290 | 0.04 | 0.05 | 0.07 |        |
| 6 | 107 | 65.4 | 3.8 | 349.0 | 320 | 1.35 | 0.42 | 0.39 | 115.82 |
|   |    |      |     | 349.0 | 291 | 0.03 | 0.04 | 0.05 |        |
| 7 | 121 | 67.9 | 3.8 | 349.5 | 322 | 1.51 | 0.46 | 0.43 | 115.66 |
|   |    |      |     | 349.5 | 290 | 0.04 | 0.04 | 0.06 |        |
| 8 | 179 | 72.5 | 3.8 | 349.5 | 320 | 1.39 | 0.42 | 0.37 | 115.06 |
|   |    |      |     | 349.6 | 295 | 0.03 | 0.03 | 0.04 |        |
| 9 | 180 | 73.4 | 3.8 | 349.5 | 320 | 1.45 | 0.44 | 0.38 | 115.18 |
|   |    |      |     | 349.6 | 295 | 0.04 | 0.04 | 0.05 |        |
| 10 | 183 | 75.5 | 3.8 | 349.0 | 320 | 1.52 | 0.44 | 0.39 | 115.27 |
|    |     |      |     | 349.0 | 296 | 0.04 | 0.04 | 0.05 |        |
| 11 | 184 | 75.5 | 3.8 | 349.0 | 320 | 1.48 | 0.42 | 0.37 | 115.12 |
|    |     |      |     | 348.9 | 296 | 0.03 | 0.04 | 0.04 |        |
| 12 | 198 | 76.6 | 3.8 | 349.5 | 324 | 1.66 | 0.48 | 0.42 | 115.01 |
|    |     |      |     | 349.5 | 295 | 0.04 | 0.04 | 0.04 |        |
| 13 | 199 | 76.4 | 3.8 | 349.6 | 324 | 1.58 | 0.47 | 0.42 | 115.22 |
|    |     |      |     | 349.5 | 292 | 0.04 | 0.04 | 0.05 |        |
| 14 | 201 | 77.2 | 3.8 | 349.5 | 326 | 1.63 | 0.48 | 0.43 | 115.42 |
|    |     |      |     | 349.5 | 292 | 0.04 | 0.04 | 0.04 |        |
| 15 | 204 | 76.6 | 3.8 | 349.5 | 326 | 1.60 | 0.47 | 0.42 | 115.20 |
|    |     |      |     | 349.5 | 291 | 0.04 | 0.04 | 0.04 |        |
| 16 | 41 | 80.0 | 3.8 | 357.9 | 324 | 1.48 | 0.50 | 0.51 | 116.2 |
|    |    |      |     | 358.0 | 285 | 0.03 | 0.04 | 0.04 |       |
| 17 | 42 | 80.0 | 3.8 | 357.9 | 324 | 1.14 | 0.44 | 0.49 | 116.9 |
|    |    |      |     | 358.0 | 285 | 0.03 | 0.04 | 0.04 |       |
| 18 | 43 | 80.0 | 3.8 | 357.9 | 324 | 1.19 | 0.46 | 0.51 | 116.6 |
|    |    |      |     | 358.0 | 284 | 0.04 | 0.04 | 0.04 |       |
| 19 | 44 | 80.0 | 3.8 | 357.9 | 320 | 1.31 | 0.48 | 0.53 | 117.0 |
|    |    |      |     | 358.0 | 290 | 0.04 | 0.04 | 0.05 |       |
| 20 | 51 | 80.0 | 3.8 | 358.0 | 324 | 1.54 | 0.54 | 0.55 | 116.8 |
|    |    |      |     | 358.0 | 289 | 0.04 | 0.04 | 0.04 |       |
| 21 | 52 | 80.0 | 3.8 | 357.9 | 324 | 1.56 | 0.55 | 0.56 | 116.7 |
|    |    |      |     | 358.0 | 290 | 0.04 | 0.04 | 0.04 |       |

TABLE 2

Results of comparative examples 1 to 9

| Comparative example | Run day | o-Xylene [g/m³ (STP)] | Air [m³ (STP)/h per tube] | Temperature of Salt bath A Salt bath B [° C.] | Temperature of PR inlet Cat. Bed [° C.] | o-Xylene MR outlet PR outlet [% by wt.] | o-Tolylaldehyde MR outlet PR outlet [% by wt.] | Phthalide MR outlet PR outlet [% by wt.] | PA yield PR outlet [m/m %] |
|---|---|---|---|---|---|---|---|---|---|
| 1 | 148 | 60.5 | 3.8 | 354.0 | 284 | 0.02 | 0.02 | 0.01 | 113.4 |
|   |     |      |     | 353.9 | 287 | 0.01 | 0.01 | 0.00 |       |
| 2 | 151 | 63.5 | 3.8 | 351.0 | 284 | 0.00 | 0.03 | 0.03 | 114.2 |
|   |     |      |     | 351.0 | 287 | 0.01 | 0.01 | 0.00 |       |
| 3 | 154 | 71.0 | 3.8 | 348.0 | 284 | 0.02 | 0.05 | 0.06 | 114.5 |
|   |     |      |     | 348.0 | 287 | 0.01 | 0.02 | 0.01 |       |
| 4 | 156 | 76.8 | 3.8 | 346.0 | 284 | 0.05 | 0.09 | 0.11 | 114.3 |
|   |     |      |     | 346.0 | 287 | 0.00 | 0.03 | 0.02 |       |
| 5 | 157 | 80.0 | 3.8 | 345.0 | 284 | 0.10 | 0.14 | 0.17 | 114.1 |
|   |     |      |     | 345.1 | 288 | 0.00 | 0.04 | 0.06 |       |
| 6 | 226 | 80.0 | 3.8 | 345.7 | 293 | 0.01 | 0.02 | 0.02 | 114.2 |
|   |     |      |     | 345.8 | 291 | 0.00 | 0.02 | 0.01 |       |
| 7 | 247 | 80.0 | 3.8 | 346.5 | 274 | 0.10 | 0.11 | 0.14 | 114.9 |
|   |     |      |     | 346.5 | 280 | 0.00 | 0.02 | 0.03 |       |
| 8 | 248 | 80.0 | 3.8 | 346.5 | 274 | 0.10 | 0.11 | 0.14 | 114.6 |
|   |     |      |     | 346.5 | 280 | 0.00 | 0.02 | 0.02 |       |

TABLE 2-continued

Results of comparative examples 1 to 9

| Comparative example | Run day | o-Xylene [g/m³ (STP)] | Air [m³ (STP)/h per tube] | Temperature of Salt bath A Salt bath B [° C.] | Temperature of PR inlet Cat. Bed [° C.] | o-Xylene MR outlet PR outlet [% by wt.] | o-Tolylaldehyde MR outlet PR outlet [% by wt.] | Phthalide MR outlet PR outlet [% by wt.] | PA yield PR outlet [m/m %] |
|---|---|---|---|---|---|---|---|---|---|
| 9 | 270 | 79.9 | 3.8 | 346.7<br>346.7 | 274<br>280 | 0.07<br>0.00 | 0.09<br>0.02 | 0.13<br>0.02 | 114.5 |

The invention claimed is:

1. A process for preparing phthalic anhydride by catalytic gas phase oxidation of o-xylene, in which a gaseous mixture of o-xylene and an oxygenous gas is converted in a main reactor to a gaseous intermediate reaction product which comprises unconverted o-xylene, phthalic anhydride underoxidation products and phthalic anhydride, the heat of reaction which arises in the main reactor being removed at least partly by indirect cooling with a heat carrier medium, and the intermediate reaction product being introduced into a postreactor with a temperature which is lower than the lowest temperature of the heat carrier medium, wherein the concentration of unconverted o-xylene in the intermediate reaction product is at least 1% by weight, and the sum of the concentrations of phthalic anhydride underoxidation products in the intermediate reaction product is at least 0.5% by weight, based in each case on the total weight of the organic components in the intermediate reaction product, and
   wherein the concentration of o-tolylaldehyde in the intermediate reaction product is at least 0.25% by weight.

2. The process according to claim 1, wherein the sum of the concentrations of o-tolylaldehyde and phthalide in the intermediate reaction product is at least 0.5% by weight.

3. The process according to claim 1, wherein the concentration of phthalide in the intermediate reaction product is at least 0.25% by weight.

4. The process according to claim 1, wherein measurements for the concentration of o-xylene are obtained in the intermediate reaction product and control interventions for the temperature of the heat carrier medium in the main reactor are formed from the measurements.

5. The process according to claim 1, wherein the o-xylene loading of the gaseous mixture which enters the main reactor is at least 60 g/m³ (STP).

6. The process according to claim 1, wherein the content of o-xylene in the intermediate reaction product is less than or equal to 20 g/m³ (STP).

7. The process according to claim 1, wherein the highest gas temperature which occurs in the postreactor is at least 30° C. lower than the highest gas temperature which occurs in the main reactor.

8. The process according to claim 1, wherein the catalysts used in the main reactor are exclusively those selected from a) one or more catalysts whose active composition is a mixed multimetal oxide comprising silver, vanadium and optionally one or more promoter metals,
   b) one or more catalysts based on vanadium oxide and titanium dioxide, in which the alkali metal content of the active composition is greater than or equal to 0.12% by weight and the phosphorus content of the active composition is less than or equal to 0.20% by weight,
   c) combinations of one or more catalysts according to the above definition a) and one or more catalysts according to the above definition b).

9. The process according to claim 1, wherein at least one catalyst based on vanadium oxide and titanium dioxide in which the alkali metal content of the active composition is less than or equal to 0.20% by weight is used in the postreactor.

10. The process according to claim 1, wherein at least some of the heat of reaction which arises in the postreactor is removed by indirect cooling with a heat carrier medium.

11. The process according to claim 1, wherein the postreactor is operated essentially adiabatically.

12. The process according to claim 1, wherein the intermediate reaction product which leaves the main reactor is cooled before it enters the postreactor.

13. The process according to claim 2, wherein the concentration of o-tolylaldehyde in the intermediate reaction product is at least 0.25% by weight.

14. The process according to claim 2, wherein the concentration of phthalide in the intermediate reaction product is at least 0.25% by weight.

15. The process according to claim 2, wherein measurements for the concentration of o-xylene are obtained in the intermediate reaction product and control interventions for the temperature of the heat carrier medium in the main reactor are formed from the measurements.

16. The process according to claim 3, wherein measurements for the concentration of o-xylene are obtained in the intermediate reaction product and control interventions for the temperature of the heat carrier medium in the main reactor are formed from the measurements.

17. The process according to claim 2, wherein the o-xylene loading of the gaseous mixture which enters the main reactor is at least 60 g/m³ (STP).

* * * * *